United States Patent [19]

Shimasaki et al.

[11] Patent Number: 6,004,775
[45] Date of Patent: Dec. 21, 1999

[54] DNA ENCODING IGFBP-4

[75] Inventors: Shunichi Shimasaki; Nicholas C. Ling, both of San Diego, Calif.

[73] Assignee: The Salk Institute for Biological Studies, La Jolla, Calif.

[21] Appl. No.: 08/110,107

[22] Filed: Aug. 20, 1993

Related U.S. Application Data

[62] Division of application No. 07/562,126, Aug. 3, 1990.

[51] Int. Cl.$^6$ .............................. C12P 21/02; C12N 15/11
[52] U.S. Cl. ................. 435/69.1; 435/252.3; 435/255.1; 435/320.1; 435/325; 536/23.5
[58] Field of Search ........................... 530/350; 536/23.5; 435/320.1, 69.1, 252.3, 240.1, 255, 255.1

[56] References Cited

U.S. PATENT DOCUMENTS

| | | | |
|---|---|---|---|
| 4,885,163 | 12/1989 | Shaar et al. | 514/2 |
| 5,212,074 | 5/1993 | Kiefer et al. | 435/69.6 |

OTHER PUBLICATIONS

Chem. et al. 1994 J. of Cellular Physiology 158:69–78.
Schmid et al. 1991 Biochemical Biophys. Res. Comm. 179(1): 579–585.
Pebonen et al. 1992. Cancer Research 52:5204–5207.
Cuatrecasar, p. 1971. Annu. Rev. Biochem. 40:259–278.
Wood et al. 1988. Molecular Endocrinology, 2(12):1176–1185.
Mohan et al. 1989. Proc. Natl. Acad. Sci. 86:8338–8342.
Shimonaka et al. Nov. 30, 1989. Biochem. Biophys. Res. Comm. 165 (1):189–195.
Lee et al. 1988. Science 239:1288–1291.
Watson, James D. 1987. *Molecular Biology of the Gene,* The Benjamin/Cummings Publishing Company, Inc, Menlo Park, CA, p. 313.

*Primary Examiner*—Charles L. Patterson, Jr.
*Attorney, Agent, or Firm*—Fitch, Even, Tabin & Flannery

[57] ABSTRACT

An insulin-like growth factor binding protein is isolated from rat serum and partially sequenced. Using nucleotide probes based upon the amino terminal sequence of the isolated protein, the complete sequence for the 233-residue rat protein, termed IGFBP-4, is deduced, and the homologous 237-residue sequence of the human protein is separately deduced. These proteins are useful in the inhibition of cell differentiation and/or proliferation requiring IGFs and are particularly useful in combating breast cancers. Antibodies to the proteins may be employed in diagnostic assays, in purification of the protein and in the modulation of bone growth.

12 Claims, 4 Drawing Sheets

FIG. 1A

```
CGGCTCGCTCTGCTCCAGCGTGCTTGCTAACTTCCCTTGGCTCCGTCCCAGCCTGCCGGG      60

GCCGCACCGTGTCCTCTCGCTCTCGGGTGTTCTCTAAGCTCTCTGGAGCTGCCTC          120

CGGGTTCCTTGCAGCCCGCTCGCGAGCCCGCTCCCCGCTCCTTGCGCCCCACCCTCGTTCT    180
                                                     -20

CACCATGCTGCCCTTCGGCCTCGTGGCCGCCCTGCTGCTGGCCGCAGGGCCTCGGCCGAG    240
       M  L  P  F  G  L  V  A  A  L  L  L  A  A  G  P  R  P  S
       -1 +1                                              +10

CCTGGGGCGACGAAGCCATCCACTGCCCTCCGTGCTCCGAGGAGAAGCTGGCCGCGCTGCCG   300
 L  G  D  E  A  I  H  C  P  P  C  S  E  E  K  L  A  R  C  R
 +20                                              +30

CCCCCCGTGGGTTGTGAGGAGCTGGTGCGGGAGCCTGGCTGCGGTTGTTGTGCCACTTG    360
 P  P  V  G  C  E  E  L  V  R  E  P  G  C  G  C  C  A  T  C
 +40                                              +50

CGCCCTGGGCTTGGGGATGCCTTGCGGGGGTGTATACACCCCACGCTGTGGCTCAGGCATGCG   420
 A  L  G  M  P  C  G  V  Y  T  P  R  C  G  S  G  M  R
 +60                                              +70

CTGCTACCCGCCCCGGGGTGGAGAAGCCCCTGCGCACATTGATGCACGGGCAAGGTGT    480
 C  Y  P  P  R  G  V  E  K  P  L  R  T  L  M  H  G  Q  G  V
 +80                                              +90

ATGCACGGAGCTGTCGGAAATCGAAGCCATCCAGGAAAGCCTGCAGACCTCTGACAAGGA    540
 C  T  E  L  S  E  I  E  A  I  Q  E  S  L  Q  T  S  D  K  D
 +100                                             +110

TGAGAGTGAGCATCCCAACAACAGCTTCAACCCCTGCAGCGCCCACGATCACAGGTGCCT    600
 E  S  E  H  P  N  N  S  F  N  P  C  S  A  H  D  H  R  C  L
```

```
                                                        +130
GCAGAAGCATATGGCCAAAGTGAGAGATCGGAGCAAGATGAAGGTTGTGGGACACCTCG  660
 Q  K  H  M  A  K  V  R  D  R  S  K  M  K  V  V  G  T  P  R
                       +140                      +150
GGAGGAACCCCGTCCTGTGCCCCAGGGTTCTTGCCAGAGCGAGCTGCACCGGGCCCTGGA  720
 E  E  P  R  P  V  P  Q  G  S  C  Q  S  E  L  H  R  A  L  E
             +160                      +170
ACGACTGGCCGCCTCGCAGAGCCGTACCCACGAAGACCTCTTCATCATCCCCATCCCCAA  780
 R  L  A  A  S  Q  S  R  T  H  E  D  L  F  I  I  P  I  P  N
       +180                      +190
CTGTGACCGCAACGGCAACTTCCACCCCAAACAGTGTCATCCTGCTCTGGATGGACAGCG  840
 C  D  R  N  G  N  F  H  P  K  Q  C  H  P  A  L  D  G  Q  R
                            +200                      +210
TGGCAAATGCTGGTGTGTGTGGATCGGAAGAGACAGGGGTGAAGCTTCCAGGGGGCTTGGAACC  900
 G  K  C  W  C  V  D  R  K  T  G  V  K  L  P  G  G  L  E  P
                      +220                      +230
CAAGGGGGAGCTGGACTGCCACCAACTGGCTGACAGCCTCCAAGAGTGAGACCTGCCAGC  960
 K  G  E  L  D  C  H  Q  L  A  D  S  L  Q  E  END
AGGTGGGGGACTCAGTGCCCCCTGAGTCCCTATGCTCTCTGGGACTGTAGAGTTGAC   1020
CTGGCATGGAGTCTTGGCCTGTCTCTGTGTGCCTCTCCTGCCCTGCCCTGCCCAAAGTTTCCC   1080
TTGGTGTGTGTGTGTGTGTGTGTTGGGATGTGCCCCACGGGGTGTGTGTGTGTGTGTG   1140
TGTGTGTGTTTATGGGATGTGCCCCACGGGGTAAACCTGAGCCTTGGCGTGCCACAGTG   1200
GGCTTAGATAGCCCAAGAGGTCTGAGTGTAGCAACAGGAAACCCCGGTGAGTTTTCAAGT   1260
CATTCTT
```

FIG. 1B

```
GGGGGGGCGCTCCCCGGCCTGCGCCCTGGCGCCCGCGCCCAGTCCTCGGGGGTCATG          60
                                                        M
                                                       -1
CTGCCCCTCTGCCTCGTGGCCGCCCTGCTGCTGGCGGCCGGGCCCGAGCCTGGGC          120
 L  P  L  C  L  V  A  A  L  L  L  A  A  G  P  G  P  S  L  G
+1                              -10                      +20
GACGAAGCCATCCACTGCCCGCCCTGCTCCGAGGAGAAGCTAGCGCGCTGCCGCCCCCCC     180
 D  E  A  I  H  C  P  P  C  S  E  E  K  L  A  R  C  R  P  P
                +30                                     +40
GTGGGCTGCGAGGAGCTGGTGCGAGAGCCGGGCGGCTGTGTGCGCCACTTGCGCCCTG        240
 V  G  C  E  E  L  V  R  E  P  G  G  C  C  A  T  C  A  L
                +50                                     +60
GGCTTGGGGATGCCCTGCGGGGTGTACACCCCCCGTTGCGGCTCGGGCCTGCGCTGCTAC     300
 G  L  G  M  P  C  G  V  Y  T  P  R  C  G  S  G  L  R  C  Y
                +70                                     +80
CCGCCCCCGAGGGGTGGAGAAGCCCTGCACACTGATGCACGGGCAAGGCGTGTGCATG        360
 P  P  P  R  G  V  E  K  P  L  H  T  L  M  H  G  Q  G  V  C  M
                +90                                     +100
GAGCTGGCGGAGATCGAGGCCATCCAGGAAAGCCTGCAGCCCCTCTGACAAGGACGAGGGT    420
 E  L  A  E  I  E  A  I  Q  E  S  L  Q  P  S  D  K  D  E  G
                +110                                    +120
GACCACCCCAACAACAGCTTCAGCCCTGTAGCGCCCATGACCGCCAGTGCCTGCAGAAG       480
 D  H  P  N  N  S  F  S  P  C  S  A  H  D  R  R  C  L  Q  K
                +130                                    +140
CACTTCGCCAAAATTCGAGACCGCAGCACCAGTGGGGCAAGATGAAGGTCAATGGGGCG       540
 H  F  A  K  I  R  D  R  S  T  S  G  G  K  M  K  V  N  G  A
                +150                                    +160
CCCCGGGAGGATGCCCGGCCTGTGCCCCAGGGCTCCTGCCAGAGCGAGCTGCACCGGGCG     600
 P  R  E  D  A  R  P  V  P  Q  G  S  C  Q  S  E  L  H  R  A
```

```
                                    +170                          +180
CTGGAGCGGCTGGCCGCTTCACAGAGCCGCACCCAGGAGACCTCTACATCATCCCCATC  620
 L   E   R   L   A   A   S   Q   S   R   T   H   E   D   L   Y   I   I   P   I
                          +190                          +200
CCCAACTGCGACCGCAACGGCAACTTCCACCCCAAGCAGTGTCACCCAGCTCTGGATGGG  720
 P   N   C   D   R   N   G   N   F   H   P   K   Q   C   H   P   A   L   D   G
                                    +210                          +220
CAGCGTGGCAAGTGCTGGTGTGTGGACCGGAAGACGGGGGTGAAGCTTCCGGGGGCCTG  780
 Q   R   G   K   C   W   C   V   D   R   K   T   G   V   K   L   P   G   G   L
                          +230
GAGCCAAAGGGGGAGCTGGACTGCCACCAGCTGGCTGACAGCTTTCGAGAGTGAGGCCTG  840
 E   P   K   G   E   L   D   C   H   Q   L   A   D   S   F   R   E  END

CCAGCAGGCCAGGGACTCAGGCGTCCCCTGCTACTCCTGTGCTCTGGAGGCTGCAGAGCTG  900
ACCCAGAGTGGAGTCTGAGTCTGCGTGCCTGCGCCCAGAAGTTCCCTCA             960
AATGCGCGTGTGCACGTGTGCGTGTGTGGTGTTTGTGAGCATGGGTGTG            1020
CCCTTGGGTAAGCCAGAGCCTGGGGTGTTCTCTTGTGTTACACAGCCCAAGAGGACT    1080
GAGACTGGCACTTAGCCCAAGAGTCTGAGCCCTGGTGTTTCCAGATCGATCCTGGAT    1140
TCACTCACTCAGCTCTAGTTTTCAGCCTTGGGAGTTTATTCTGACTTCCTCTGATTTG    1200
CTACGTGCCAGCTCTAGACACTCCTATAAGGAGAAGAGACATGTCAAGCCTGTGGGAGTTACCTTGACCATCGTCTTCCTCTCAAGCTAGCCA 1320
GCATGTGAGACTCAGAGGAGAAGAGACATGTCAAGCCTGTGGGAGTAGAAAATCTCATTC 1260
CCAGAGTCAGAGGAGAAGAGACTACCTTGACCATCGTCTTCCTCTCAAGCTAGCCA    1380
GAGGGTGGGAGCCTAAGGAAGCGTGGGGTAGCAGATGAGTGAGTCCTCTCTGCACGAGGTCCTCCTTCCT 1500
CCCACTCCCAAAGCTCAGACTTGCCAGGCTCCTGCTTGGTTGGCTGCAGCTTGCTGTGGCT 1440
TAGGTCTGGTGTTGTTGCACCATCATCTGTTGGCACCATCAGCCCTGCTGTGAAGGAGAGCCTCCAGAGCCCTGCTGTGTGGA 1560
GAGCCAAGGGGTCAAAGGGGTCAGGGGATGGGAAGAAAGAGAGGGGCTTCCTGGGCTCGT 1620
CTCTGAGCAGTCAGGTGCTAGGGATGAAGTCACCGGATGAACCTACACCTCCCCTACACCTCCCCTTCCAGTGCTCCCTGTAGCTC 1680
AAGACCCAGCCATGAAGTCACCGGATGAACCTATCCTTCCCCCTACACCTCCCCTACTCCCCT 1740
TGCCTCCCTCCATATCTCCTTCCCCGTACACACCACCCACACCTCCCCTACTCCCCT    1860
GGGCATCTTCTGGCTTGACTGACTGGATGAAGGAGACTTAGG                   1800
```

DNA ENCODING IGFBP-4

This is a division of application Ser. No. 07/562,126 filed Aug. 3, 1990.

This invention was made with Government support under Grant No. HD-09690, and Contract NO1-HD-0-2902, awarded by the NICHD, one institute of the National Institutes of Health. The Government has certain rights in this invention.

This invention relates to controlling the effects of insulin-like growth factors (IGFs) in mammals and more particularly to novel insulin-like growth factor binding proteins which can be employed to complex IGFs and thereby modulate IGF actions.

BACKGROUND OF THE INVENTION

Two insulin-like growth factors (IGF-I and IGF-II) are presently known to exist and to be required for the proliferation of various cells. For example, the topical use of IGF-II for wound-healing is taught in U.S. Pat. No. 4,885,163 (Dec. 5, 1989). It is also reported that IGFs have a particular effect upon the growth of cells of mesodermal origin and on their differentiation, and further, that the IGFs exhibit potency in stimulating DNA synthesis in human fibroblasts and in rat osteoblasts. In addition, it is suggested that IGF-I may serve to stimulate collagen synthesis in human fibroblasts, whereas studies report that IGF-II may have a predominant role in undifferentiated cell proliferation.

Several proteins have been discovered which bind to these IGFs and modulate IGF actions either in an inhibitory or a stimulatory manner, and these proteins are termed insulin-like growth factor binding proteins (IGFBPs).

Insulin-like growth factors (IGF-I and IGF-II) are synthesized by multiple tissues and circulate in plasma to modulate the growth of various cell types. They do not exist in the blood as free hormones but are bound to carriers in the form of IGFBPs. To date three distinct classes of IGFBPs have been characterized, based on their complete primary structure having been obtained by molecular cloning, all of which are able to bind both IGF-I and IGF-II and to modulate IGF actions either in an inhibitory or a stimulatory manner.

Based on the recommendation proposed by an IGFBP conference held in Vancouver, Canada in June 1989, the first BP class whose complete primary structure was deduced has been named IGFBP-1; its structure was deduced from cDNA clones identified in the libraries prepared front a human HEP-G2 hepatoma cell line, from human placenta and from both human and rat decidua. A human genomic clone encoding IGFBP-1 was also isolated and characterized (Brinkman, A., et al., *B.B.R.C.* 157, 898–907 (1989)), the gene locus of which is mapped at location p12–p13 on chromosome 7, Alitalo, T. et al., *Hum. Genet.* 83, 335–338 (1989). This protein exhibits a molecular weight ($M_r$) of 28 kDa on SDS/PAGE under non-reducing conditions and has almost equal binding affinity for IGF-I and IGF-II. It contains no potential N-linked glycosylation sites, but it has at least five potential O-linked glycosylation sites, which may account for a reported 4.3% carbohydrate content of the protein. The circulating level of the IGFBP-1 is elevated in patients and animals with insulin-dependent diabetes mellitus.

The second BP class is one for which the complete primary structure was deduced from cDNAs isolated from a rat BRL-3A cell library as well as from adult rat and human fetal liver libraries; it has been named IGFBP-2. This BP, having $M_r$ of 31.5–33.0 kDa on SDS/PAGE under non-reducing conditions, exhibits equal affinity for IGF-I and IGF-II when IGF-I is used as a radioligand, but it shows a marked preference for IGF-II when the radioligand is IGF-II. The level of IGFBP-2 in rat serum is high in fetus but decreases in adult. The physiological role of IGFBP-2 is not well known, but Adashi et al. *Endocrinologqy*, 126, 1305–1307 (1990) recently reported that pituitary follicle-stimulating hormone (FSH) inhibits the constitutive release of IGFBP-2 from rat ovarian granulosa cells.

The third BP class is a high molecular weight IGFBP within the 150 kDa IGF-binding complex found in plasma. Its complete primary structure was deduced from human, porcine and rat cDNAs, and it has been named IGFBP-3, see Shimasaki, S., et al., *B.B.R.C.*, 165, 907–912 (1989). This 150 kDa complex consists of three components, an IGFBP-3 of 53 kDa bound to an IGF and an acid-labile 80 kDa protein which can only bind to IGFBP-3 in association with IGF under neutral conditions. Both the 53 kDa IGFBP-3 and the 80 kDa acid-labile subunits are glycosylated. Moreover, the circulating level of the complex is dependent on growth hormone (GH). This protein has recently been isolated from ovarian follicular fluid, and it appears to act as an inhibitor to the FSH-stimulated production of estradiol in cultures of rat ovarian granulosa cells.

Besides these three IGFBPs, it is believed that other BPs for IGF exist.

SUMMARY OF THE INVENTION

A novel IGFBP has been isolated from rat serum, and subsequently, the cDNAs encoding the complete primary structure of this protein have been isolated and characterized from both the rat and the human species. The deduced amino acid sequences of the cDNAs reveal a mature polypeptide of 233 amino acids for the rat protein, while the human protein is a homologous polypeptide of 237 amino acid residues (containing an additional 4 amino acid sequence in the central region of the molecule compared to the rat protein). It is hereinafter referred to as IGFBP-4. These rat and human proteins bind to both IGF-I and IGF-II and can be administered as anti-neoplastic agents along with an appropriate pharmaceutically or veterinarially acceptable carrier for various therapeutic purposes, such as the inhibition of cell differentiation and/or proliferation requiring IGFs. For example, IGFBP-4 can be used to combat breast cancers and other tissues having a high IGF requirement, and in addition, it is expected to be useful for modulating bone growth.

BRIEF DESCRIPTION OF THE DRAWINGS

FIGS. 1A and 1B show the nucleotide and deduced amino acid sequence of rat IGFBP-4 as determined by sequencing a cDNA clone. The nucleotides are numbered at the right, and the amino acids, in one-letter code, are numbered throughout. A potential Asn-linked glycosylation site at position 104 is marked by an asterisk.

FIGS. 2A and 2B show the nucleotide and deduced amino acid sequence of human IGFBP-4 as determined by sequencing a cDNA clone. The nucleotides are numbered at the right, and the amino acids, in one-letter code, are numbered throughout. The potential Asn-linked glycosylation site at position 104 is marked by an asterisk.

DETAILED DESCRIPTION OF THE PREFERRED EMBODIMENTS

IGFBP-4 was isolated and purified from rat serum using techniques generally similar to those described in Shimonaka, M. et al., *B.B.R.C.*, 165, 189–195 (1989); thereafter, sequencing of the amino terminus of the purified protein was carried out to obtain the sequence of the first 40 amino acid residues. In this manner, it was determined that the amino terminus of the rat protein had the following sequence:
Asp-Glu-Ala-Ile-His-Xaa-Pro-Pro-Xaa-Ser-Glu-Glu-Lys-Leu-Ala-Arg-Xaa-Arg-Pro-Pro-Val-Gly-Xaa-Glu-Glu-Leu-Val-Arg-Glu-Pro-Gly-Xaa-Gly-Xaa-Xaa-Ala-Thr-Xaa-Ala-Leu. Based upon the evident homology between this protein and the other 3 known IGFBP structures, it was assumed that the unidentified amino acid residue (Xaa) was cysteine (Cys).

The amino acids are referred to herein using either the standard 3-letter or 1-letter designations as follows:

| NAME | 3-LETTER | 1-LETTER |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

It appeared that the predicted DNA sequence in this amino-terminal region, based upon the frequently utilized eukaryotic codons, would comprise about 70% of the nucleotides G and C. Because such a high G- and C-rich probe would likely yield many nonspecific hybridizations, it was decided to utilize the polymerase chain reaction (PCR) technology to determine a nucleotide sequence for this region. Accordingly, two synthetic oligonucleotide primers for PCR were designed which incorporated all possible codon combinations encoding (a) the 8-amino acid residue sequence at the N-terminus (Asp-Glu-Ala-Ile-His-Cys-Pro-Pro) and (b) the 8-amino acid residue sequence which appears at the carboxy-terminus of this 40-residue sequence (i.e. Cys-Gly-Cys-Cys-Ala-Thr-Cys-Ala). The synthetic primer mixtures are as follows:
5'-GA(CT)GA(AG)GC(ACGT)AT(ACT)CA(CT)TG(CT)CC(ACGT)CC-3' and
5'-GC(AG)CA(ACGT)GT(ACGT)GC(AG)CA(AG)CA(ACGT)CC(AG)CA-3'

PCR was performed by an Ericomp TwinBlock™ system (San Diego, Calif.) with GeneAmp™ DNA Amplification Reagent Kit (Perkin Elmer Cetus, Norwalk, Conn.) using a rat liver cDNA library (Clontech Laboratories, Palo Alto, Calif.) as a template. Annealing reactions were performed at 60° C. for 30 sec., followed by a 30 sec. extension at 72° C. and 15 sec. denaturation at 94° C. After 35 cycles of amplification, a PCR-extended fragment of 116 bp was purified, kinased by ATP and then cloned into EcoRV site of pBluescript SK+ (Stratagene, San Diego, Calif.). The DNA sequence of the PCR-amplified cDNA fragment was determined by the double-stranded dideoxy-chain-termination method using Sequenase (United States Biochem. Co., Cleveland, Ohio); its deduced amino acid sequence matched with that obtained by protein sequencing.

This PCR-amplified cDNA fragment having the expected 116 bp length obtained from the rat liver cDNA library was thereafter used as a probe, after $^{32}$P-labeling, to screen the rat liver cDNA library.

After labeling by a random priming method using $^{32}$P-dCTP, the PCR-amplified DNA fragment was used to isolate cDNA clones encoding rat IGFBP-4. The same rat liver cDNA library used for the PCR was then screened with this probe, and three positive clones were obtained. These clones were sequenced, and the results revealed that all three of them contained the complete coding region including the signal sequence.

The cDNA inserts from the positive clones were excised with EcoRI and inserted into pBluescript SK+. The DNA sequences were determined for both strands by successive extension along a template DNA by primer-directed double-stranded dideoxy sequencing using synthetic oligonucleotides (17-mers) based on the sequence at the 3' end of a region already sequenced.

The complete DNA sequence of one clone is shown in FIG. 1 together with its predicted amino acid sequence. The amino-terminal residue of the 233-residue mature protein is denoted by +1 so as to be in agreement with the amino-terminal residue of the purified rat IGFBP-4. The preceding 21 amino acid sequence from the amino-terminal residue of the mature protein fits a typical signal peptide sequence; it has a central region rich in hydrophobic amino acids with large side-chains and terminates in a neutral residue with a small side-chain which, in this case, is Gly at position −1.

The insert fragment of this clone was excised and subsequently used as a probe to identify the corresponding human IGFBP-4 clone. A human placenta cDNA library in phages consisting of $2.4 \times 10^6$ independent clones was screened with the rat IGFBP-4 probe, and 132 positive clones were obtained out of a half million independent phages. Ten positive clones were then randomly selected and purified, and the insert DNAs were prepared. After examining the length of their inserts, the 4 longest clones were chosen and subcloned into the EcoRI site of pBluescript SK+for DNA sequence determination. The complete DNA sequence of one clone as well as its deduced amino acid sequence are shown in FIG. 2. The open reading frame of this clone encodes a protein of 258 amino acids which includes a signal sequence of 21 residues based on homology with the rat sequence.

The amino acid sequence comparison between rat and human IGFBP-4 is shown in TABLE 1 wherein amino acids are shown in one-letter code, and only amino acids that differ from human IGFBP-4 are presented in the rat structure. The mature form of rat IGFBP-4 consists of 233 amino acids, whereas the human homolog is 4 amino acids longer.

TABLE 1

```
              10        20        30        40        50        60        70        80
              .         .         .         .         .         .         .         .
human  DEAIHCPPCSEEKLARCRPPVGCEELVREPGCGCCATCALGLGMPCGVYTPRCGSGLRCYPPRGVEKPLHTLMHGQGVCM
rat                                                           M         R         T 90       100       110       120       130       140       150       160
              .         *         .         .         .         .         .         .
human  ELAEIEAIQESLQTSDKDEGDHPNNSFSPCSAHDRRCLQKHFAKIRDRSTSGGKMKVNGAPREDARPVPQGSCQSELHRA
rat         S            SE      N       H       M V   ----   V T    EP 170       180       190       200       210       220       230
              .         .         .         .         .         .         .
human  LERLAASQSRTHEDLYIIPIPNCDRNGNFHPKQCHPALDGQRGKCWCVDRKTGVKLPGGLEPKGELDCHQLADSFRE
rat                  F                                                        LQ
```

The proteins are highly homologous, with approximately 8% amino acid substitutions between the two species. Gaps at positions 130–133 are inserted in the rat sequence to allow maximal homology alignment. The location of all the cysteines are conserved, as is the single potential N-linked glycosylation site, which is marked by an asterisk. The most substituted region appears in the mid-portion of the molecule where an additional 4 amino acid sequence is present in the human structure.

Antibodies to these IGFBP-4 proteins of either monoclonal or polyclonal form can be produced using techniques presently known in the art, and antibodies which are effective to counteract the effects of IGFBP-4 can be elicited using only the synthetic N-terminal segment of the rat protein. For example, antibodies raised in rabbits against a synthetic peptide, representing the amino terminal sequence of the IGFBP-4, recognize the synthetic peptide and the IGFBP-4 on an equimolar basis, and they are capable of inhibiting the activity of the native protein in vitro. Amino terminal-directed antibodies to IGFBP-4 may be obtained by immunizing three month old male and female white New Zealand rabbits with the synthetic peptide to which Tyr has been added at the C-terminus in order to couple it, as an antigen, to BSA by a bisdiazotized benzidine(BDB) linkage by reaction for 2 hours at 4° C. The reaction mixture is dialized to remove low molecular weight material, and the retentate is frozen in liquid nitrogen and stored at −20° C. Animals are immunized with the equivalent of 1 mg of the peptide antigen according to the procedure of Benoit et al. *P.N.A.S. USA,* 79, 917–921 (1982). At four week intervals, the animals are boosted by injections of 200 μg of the antigen and bled ten to fourteen days later. After the third boost, antiserum is examined for its capacity to bind radioiodinated antigen peptide prepared by the chloramine-T method and then purified by CMC-ion exchange column chromatography.

A radioimmunoassay is established with the antisera and serum from subsequent bleeds from the same rabbits. The native protein is recognized by the antibodies on an equimolar basis as compared to the synthetic peptide antigen. These antibodies are considered to be capable of at least partially neutralizing the biological activity of the IGFBP-4, and substantially all such activity can likely be neutralized when higher amounts of antibodies are used. It is believed that immunoaffinity or affinity chromatography can also be applied to achieve the purification of IGFBP-4 from serum or of biological materials.

These antibodies can be used in assays for detecting the levels of IGFBP-4 in mammals, particularly humans. The antibodies can also be used for treatment to neutralize the effect of IGFBP-4 in mammals and should also prove to be quite useful for diagnostic test kits and the like.

From presently available evidence, it is most likely that there is internal disulfide-bonding between cysteine residues of the chain. Mammalian IGFBP-4 polypeptides produced by recombinant DNA techniques are inherently biologically active, perhaps because the three-dimensional structure which the IGFBP-4 assumes within cells is the structure recognized by the receptor. The three-dimensional structure which the molecule assumes through natural folding and through hydrophobic and hydrophilic interactions with aqueous media may promote desired bonding or non-bonding between cysteine residues. Also, enzymatic regulatory mechanisms within cells may help to ensure desired disulfide bonding or non-bonding, either by preventing bonding or by directing disulfide bonding between particular cysteine residues. Enzymes might also cleave "incorrect" bonding to enable the molecule to reorientate itself and assume the correct natural structure. Cysteine residues that are not internally bonded may be disulfide-bonded to free cysteine moieties. The three-dimensional structure of the molecule may also be such that random bonding or non-bonding of cysteine residues, either with each other or to free cysteines, does not substantially affect the biological structure of the protein molecule.

To synthesize a protein having the mammalian IGFBP-4 amino acid residue sequence by recombinant DNA, a double-stranded DNA chain which encodes IGFBP-4 might be synthetically constructed. Although it is nowadays felt that PCR techniques would be method of choice to produce DNA chains, a DNA chain encoding IGFBP-4 could be designed using certain particular codons that are more efficient for polypeptide expression in a certain type of organism, i.e. selection might employ those codons which are most efficient for expression in the type of organism which is to serve as the host for the recombinant vector. However, any correct set of codons will encode a desired product, although perhaps slightly less efficiently. Codon selection may also depend upon vector construction considerations; for example, it may be necessary to avoid placing a particular restriction site in the DNA chain if, subsequent to inserting the synthetic DNA chain, the vector is to be manipulated using the restriction enzyme that cleaves at such a site. Also, one should avoid placing restriction sites in the DNA chain if the host organism, which is to be transformed with the recombinant vector containing the DNA chain, is known to produce a restriction enzyme that would cleave at such a site within the DNA chain.

To assemble a synthetic IGFBP-4-encoding DNA chain, oligonucleotides are constructed by conventional procedures such as those described in T. Maniatis et al., *Cold Spring Harbor Laboratory Manual*, Cold Spring Harbor, New York (1982) (hereinafter, *CSHLM*). Sense and antisense oligonucleotide chains, up to about 70 nucleotide residues long, are synthesized, preferably on automated synthesizers, such as the Applied Biosystem Inc. Model 380A DNA synthesizer. The oligonucleotide chains are constructed so that portions of the sense and antisense oligonucleotides overlap, associating with each other through hydrogen bonding between complementary base pairs and thereby forming double stranded chains, in most cases with gaps in the strands. Subsequently, the gaps in the strands are filled in, and oligonucleotides of each strand are joined end to end with nucleotide triphosphates in the presence of appropriate DNA polymerases and/or with ligases.

As an alternative to such stepwise construction of a synthetic DNA chain, the cDNA corresponding to IGFBP-4 that was cloned to deduce the complete structure of IGFBP-4 is used. As is well known, a cDNA library or an expression library is produced in a conventional manner by reverse transcription from messenger RNA (mRNA) from a suitable IGFBP-4-producing mammalian cell line or tissue. To select clones containing IGFBP-4 sequences, the hybridization probe obtained by PCR technology (or mixed probes which accommodate the degeneracy of the genetic code and correspond to a selected portion of the IGFBP-4 protein are produced) is used to identify clones containing such sequences. Screening of such an expression library with IGFBP-4 antibodies may also be used, either alone or in conjunction with hybridization probing, to identify or confirm the presence of IGFBP-4-encoding DNA sequences in cDNA library clones which are expressing IGFBP-4. Such techniques are taught, for example in *CSHLM*, supra.

In addition to the IGFBP-4-encoding sequences, a DNA chain should contain additional sequences depending upon vector construction considerations. Typically, a synthesized DNA chain has linkers at its ends to facilitate insertion into restriction sites within a cloning vector. A DNA chain may be constructed so as to encode the IGFBP-4 amino acid sequences as a portion of a fusion polypeptide; and if so, it will generally contain terminal sequences that encode amino acid residue sequences that serve as proteolytic processing sites, whereby the IGFBP-4 polypeptide may be proteolytically cleaved from the remainder of the fusion polypeptide. The terminal portions of the synthetic DNA chain may also contain appropriate start and stop signals.

Accordingly, a double-stranded IGFBP-4-encoding DNA chain is constructed or modified with appropriate linkers for its insertion into a particular appropriate cloning vector. The cloning vector that is to be recombined to incorporate the DNA chain is selected appropriate to its viability and expression in a host organism or cell line, and the manner of insertion of the DNA chain depends upon factors particular to the host. For example, if the DNA chain is to be inserted into a vector for insertion into a prokaryotic cell, such as *E. coli*, the DNA chain will be inserted 3' of a promoter sequence, a Shine-Delgarno sequence (or ribosome binding site) that is within a 5' non-translated portion and an ATG start codon. The ATG start codon is appropriately spaced from the Shine-Delgarno sequence, and the encoding sequence is placed in correct reading frame with the ATG start codon. The cloning vector also provides a 3' non-translated region and a translation termination site. For insertion into a eukaryotic cell, such as a yeast cell or a cell line obtained from a higher animal, the IGFBP-4-encoding oligonucleotide sequence is appropriately spaced from a capping site and in correct reading frame with an ATG start signal. The cloning vector also provides a 3' non-translated region and a translation termination site.

Prokaryotic transformation vectors, such as pBR322, pMB9, Col E1, pCR1, RP4 and lambda-phage, are available for inserting a DNA chain of the length which encodes IGFBP-4 with substantial assurance of at least some expression of the encoded polypeptide. Typically, such vectors are constructed or modified to have one or more unique restriction sites appropriately positioned relative to a promoter, such as the lac promoter. The DNA chain may be inserted with appropriate linkers into such a restriction site, with substantial assurance of production of IGFBP-4 in a prokaryotic cell line transformed with the recombinant vector. To assure proper reading frame, linkers of various lengths may be provided at the ends of the IGFBP-4-encoding sequences. Alternatively, cassettes, which include sequences, such as the 5' region of the lac Z gene (including the operator, promoter, transcription start site, Shine-Delgarno sequence and translation initiation signal), the regulatory region from the tryptophane gene (trp operator, promoter, ribosome binding site and translation initiator), and a fusion gene containing these two promoters called the trp-lac or commonly called the Tac promoter are available into which the synthetic DNA chain may be conveniently inserted and then the cassette inserted into a cloning vector of choice.

Similarly, eukaryotic transformation vectors, such as, the cloned bovine papilloma virus genome, the cloned genomes of the murine retroviruses, and eukaryotic cassettes, such as the pSV-2 gpt system (described by Mulligan and Berg, *Nature* 277, 108–114, 1979), the Okayama-Berg cloning system (*Mol. Cell Biol.* 2, 161–170, 1982), and the expression cloning vector recently described by Genetics Institute (*Science* 228, 810–815, 1985), are available which provide substantial assurance of at least some expression of IGFBP-4 in the transformed eukaryotic cell line.

As previously mentioned, a convenient way to ensure production of IGFBP-4 or a protein of a similar length is to produce the protein initially as a segment of a gene-encoded fusion protein. In such case, the DNA chain is constructed so that the expressed protein has enzymatic processing sites flanking the IGFBP-4 amino acid residue sequences. A IGFBP-4-encoding DNA chain may be inserted, for example, into the beta-galactosidase gene for insertion into *E. coli*, in which case, the expressed fusion protein is subsequently cleaved with proteolytic enzymes to release the IGFBP-4 from beta-galactosidase peptide sequences.

An advantage of inserting the IGFBP-4-encoding sequence so that the IGFBP-4 sequence is expressed as a cleavable segment of a fusion protein, e.g. as the IGFBP-4 sequence fused within the beta-galactosidase peptide sequence, is that the endogenous protein into which the IGFBP-4 sequence is inserted is generally rendered non-functional, thereby facilitating selection for vectors encoding the fusion protein.

The IGFBP-4 protein may also be reproduced in yeast using known recombinant DNA techniques. For example, plasmid pIGFBP-4, amplified in a pIGFBP-4-producing *E. coli* clone, is isolated and cleaved with Eco RI and Sal I. This digested plasmid is electrophoresed on an agarose gel allowing for the separation and recovery of the amplified bIGFBP-4 insert. The insert is inserted into the plasmic pYEp, a shuttle vector which can be used to transform both *E. coli* and *Saccharomyces cerevisiae* yeast. Insertion of the synthetic DNA chain at this point assures that the DNA sequence is under the control of a promoter, in proper reading frame from an ATG signal and properly spaced relative to a cap site. The shuttle vector is used to transform URA3, a strain of *S. cerevisiae* yeast from which the oratate monophosphate decarboxylase gene is deleted.

The transformed yeast is grown in medium to attain log growth. The yeast is separated from its culture medium, and cell lysates are prepared. Pooled cell lysates are determined by RIA to be reactive with antibody raised against IGFBP-4, demonstrating that a protein containing IGFBP-4 protein segment is expressed within the yeast cells.

The production of IGFBP-4 can be carried out in both prokaryotic and eukaryotic cell lines to provide protein for biological and therapeutic use. While IGFBP-4 synthesis is easily demonstrated using either bacteria or yeast cell lines, the synthetic genes should be insertable for expression in cells of higher animals, such ;as mammalian tumor cells. Such mammalian cells may be grown, for example, as peritoneal tumors in host animals, and IGFBP-4 harvested from the peritoneal fluid.

Although the above examples demonstrate that IGFBP-4 can be synthesized through recombinant DNA techniques, the examples do not purport to have maximized IGFBP-4 production. It is expected that subsequent selection of more efficient cloning vectors and host cell lines will increase the yield of IGFBP-4. Known gene amplification techniques for both eukaryotic and prokaryotic cells may be used to increase production of IGFBP-4. Secretion of the gene-encoded protein from the host cell line into the culture medium is also considered to be an important factor in obtaining synthetic IGFBP-4 in large quantities.

The availability of such mammalian IGFBP-4 proteins permit their use to complex and neutralize IGFs and these proteins should be useful in the treatment of conditions which are caused by an overabundance of IGFs, for example, certain types of breast cancer. Administration of substantially pure monoclonal antibodies to IGFBP-4 have potential therapeutic applications to treat cases where it is desired to counteract the binding of IGFs, for example, in the modulation of bone growth.

Substantially pure IGFBP-4 protein can be routinely obtained having significantly higher purity than IGFBP-4 that is extracted from mammalian serum. IGFBP-4 proteins constitute only minor constituents of normal mammalian serum, being present in only very impure form, relative to other native proteins also present. Recombinant DNA techniques, for example, can be used to generate organisms or cell lines that produce the heterologous protein in significantly higher proportions relative to total protein, in the cellular material and/or the secretions thereof, than the proportions at which native IGFBP-4 are present. Because the starting material from which such synthetic IGFBP-4 proteins are isolated has a substantially greater concentration of the heterologous protein, purification techniques can fairly simply produce more highly purified IGFBP-4 fractions. Using appropriate isolation techniques, it is possible to routinely obtain IGFBP-4 proteins which are at least about 95% pure (by weight of total proteins) and which is herein referred to as substantially pure.

The protein should be administered under the guidance of a physician, and pharmaceutical compositions will usually contain the protein in conjunction with a conventional, pharmaceutically-acceptable carrier. For treatment, substantially pure synthetic IGFBP-4 or the nontoxic salts thereof, combined with a pharmaceutically acceptable carrier to form a pharmaceutical composition, are administered to mammals, including humans, either intravenously, subcutaneously, intramuscularly or orally. The required dosage will vary with the particular treatment and with the duration of desired treatment; however, it is anticipated that dosages between about 10 micrograms and about 1 milligram per kilogram of body weight per day will be used for therapeutic treatment. Antibodies are administered in proportionately appropriate amounts in accordance with known practices in this art.

Such protein may be administered in the form of pharmaceutically acceptable nontoxic salts, such as acid addition salts or metal complexes, e.g., with zinc, iron or the like (which are broadly considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

It may also be desirable to deliver IGFBP-4 over prolonged periods of time, for example, for periods of one week to one year from a single administration, and slow release, depot or implant dosage forms may be utilized. For example, a dosage form may contain a pharmaceutically acceptable non-toxic salt of the compound which has a low degree of solubility in body fluids, for example, an acid addition salt with the polybasic acid; a salt with a polyvalent metal cation; or combination of the two salts. A relatively insoluble salt may also be formulated in a gel, for example, an aluminum stearate gel. A suitable slow release depot formulation for injection may also contain IGFBP-4 or a salt thereof dispersed or encapsulated in a slow degrading, non-toxic or non-antigenic polymer such as a polylactic acid/polyglycolic acid polymer, for example, as described in U.S. Pat. No. 3,773,919. These compounds may also be formulated into silastic implants.

For purposes of this application, mammalian IGFBP-4 proteins should be considered to constitute proteins having the amino acid residue sequences set forth hereinbefore as well as naturally occurring amino acid sequence variants of other mammalian species and fragments of the foregoing having equivalent biological activity. Unless otherwise stated hereinbefore, all percentages are volume percents.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, biologically active fragments of most proteins, shortened either at the C-terminus or at the N-terminus, can be employed instead of the entire protein.

Particular features of the invention are emphasized in the claims which follow.

What is claimed is:

1. An isolated DNA sequence comprising a nucleotide sequence encoding an IGFBP-4 having the amino acid sequence:

```
D E A I H C P P C S E E K L A R C R P P

V G C E E L V R E P G C G C C A T C A L

G L G M P C G V Y T P R C G S G L R C Y

P P R G V E K P L H T L M H G Q G V C M

E L A E I E A I Q E S L Q P S D K D E G

D H P N N S F S P C S A H D R R C L Q K
```

-continued

```
H F A K I R D R S T S G G K M K V N G A

P R E D A R P V P Q G S C Q S E L H R A

L E R L A A S Q S R T H E D L Y I I P I

P N C D R N G N F H P K Q C H P A L D G

Q R G K C W C V D R K T G V K L P G G L

E P K G E L D C H Q L A D S F R E
``` or the amino acid sequence:

```
D E A I H C P P C S E E K L A R C R

P P V G C E E L V R E P G C G C C A T C

A L G L G M P C G V Y T P R C G S G M R

C Y P P R G V E K P L R T L M H G Q G V

C T E L S E I E A I Q E S L Q T S D K D

E S E H P N N S F N P C S A H D H R C L

Q K H M A K V R D R S K M K V V G T P R

E E P R P V P Q G S C Q S E L H R A L E

R L A A S Q S R T H E D L F I I P I P N

C D R N G N F H P K Q C H P A L D G Q R

G K C W C V D R K T G V K L P G G L E P

K G E L D C H Q L A D S L Q E.
```

2. The isolated DNA of claim 1 which encodes a protein precursor comprising the 258 amino acid residues of FIG. 2.

3. The isolated DNA of claim 1 wherein there are no interruptions by introns.

4. The isolated DNA of claim 1 having the nucleotide sequence set forth in FIG. 2.

5. A replicable recombinant DNA expression vector which includes the DNA of claim 1, said vector being capable of expressing the DNA in a microorganism or cell culture wherein said vector is inserted.

6. The vector of claim 5 wherein, upon expression, the protein of the amino acid sequence 1–237 of FIG. 2 is produced.

7. Recombinant host cells transformed with the vector of claim 5.

8. A method of producing an IGFBP-4, which method comprises culturing host cells of claim 7 under conditions which permit the expression of the DNA and recovering the IGFBP-4 protein produced.

9. The method of claim 8 wherein the host cells are either bacteria or mammalian cells.

10. A microorganism transformed with the vector of claim 5, said microorganism being capable of expressing the DNA encoding the IGFBP-4.

11. A cell culture capable of expressing DNA encoding an IGFBP-4 protein, which cell culture is obtained by transforming a cell line with the vector of claim 5.

12. A method of producing an IGFBP-4 protein, which method comprises growing the cell culture of claim 11 under conditions permitting expression of the DNA of said vector and recovering the IGFBP-4 protein produced.

* * * * *